United States Patent [19]

Schwartz

[11] Patent Number: 4,918,004
[45] Date of Patent: * Apr. 17, 1990

[54] METHOD OF CALIBRATING A FLOW CYTOMETER OR FLUORESCENCE MICROSCOPE FOR QUANTITATING BINDING ANTIBODIES ON A SELECTED SAMPLE, AND MICROBEAD CALIBRATION KIT THEREFOR

[75] Inventor: Abraham Schwartz, Durham, N.C.

[73] Assignee: Caribbean Microparticles Corporation, Hato Rey, P.R.

[ * ] Notice: The portion of the term of this patent subsequent to May 9, 2006 has been disclaimed.

[21] Appl. No.: 131,200

[22] Filed: Dec. 10, 1987

Related U.S. Application Data

[63] Continuation-in-part of Ser. No. 128,786, Dec. 4, 1987, Pat. No. 4,857,451, and Ser. No. 850,746, Apr. 11, 1986, Pat. No. 4,828,984, said Ser. No. 128,786, is a continuation-in-part of Ser. No. 805,654, Dec. 11, 1985, Pat. No. 4,774,189, which is a continuation-in-part of Ser. No. 685,464, Dec. 24, 1984, Pat. No. 4,774,180.

[51] Int. Cl.$^4$ ............... G01N 33/546; G01N 33/547
[52] U.S. Cl. .......................................... 435/7; 435/29; 435/34; 435/810; 436/10; 436/510; 436/512; 436/533; 436/534; 436/548; 436/800; 436/811
[58] Field of Search ............... 435/7, 29, 34, 810; 436/10, 512, 533, 534, 548, 800, 510, 811

[56] References Cited

U.S. PATENT DOCUMENTS

4,814,323  3/1989  Andrieu et al. ............... 514/885
4,828,984  5/1989  Schwartz ....................... 436/519

Primary Examiner—Sam Rosen
Assistant Examiner—David A. Saunders
Attorney, Agent, or Firm—Olive & Olive

[57] ABSTRACT

A method for calibrating a flow cytometer or fluorescence microscope in terms of number of binding antibodies as a function of fluorescence intensity value measured on the flow cytometer or fluorescence microscope, and subsequent measuring of a sample to which the antibodies are bindable. Also disclosed is a microbead calibration kit for carrying out the calibration method of the invention. The disclosed calibration methodology provides a direct relationship between instrument response and numbers of binding antibodies, independent of the fluorochrome employed to label the samples being measured. The method has utility in monitoring the status of an antigenic cellular condition in which the number of antibodies binding to successively obtained cellular samples is determined, to establish the progressionary character of the antigenic cellular condition, in a host from which the cellular samples are taken.

19 Claims, 1 Drawing Sheet

METHOD OF CALIBRATING A FLOW CYTOMETER OR FLUORESCENCE MICROSCOPE FOR QUANTITATING BINDING ANTIBODIES ON A SELECTED SAMPLE, AND MICROBEAD CALIBRATION KIT THEREFOR

CROSS REFERENCE TO RELATED APPLICATIONS

This application is a continuation-in-part of U.S. application No. 07/128,786 filed Dec. 4, 1987, and issued Aug. 15, 1989 as U.S. Pat. No. 4,857,451, which in turn is a continuation-in-part of U.S. application No. 06/805,654 filed Dec. 11, 1985, and issued Sept. 27, 1988 as U.S. Pat. No. 4,774,189, which in turn is a continuation-in-part of U.S. application No. 06/685,464 filed Dec. 24, 1984, and issued Sept. 27, 1988 as U.S. Pat. No. 4,774,180; this application is also a continuation-in-part of U.S. application No. 06/850,746 filed Apr. 11, 1986, and issued May 9, 1989 as U.S. Pat. No. 4,828,984.

BACKGROUND OF THE INVENTION

1. Field of The Invention

This invention relates generally to a method for calibrating a flow cytometer or fluorescence microscope in terms of number of binding antibodies as a function of fluorescence Intensity value measured on the flow cytometer or fluorescence microscope, and subsequently measuring a sample to which such antibodies are bindable. The invention also relates to a microbead calibration kit suitable for carrying out such calibration method.

2. Background and Description of the Art

The development of monoclonal antibodies as analytical probes for the detection of cell surface antigen expression combined with the establishment of sophisticated techniques such as flow cytometry have greatly contributed to improve the clinical diagnosis and medical treatment of a variety of immunological diseases. The identification of a particular sub-type of cell, even when present in minuscule numbers (e.g. B cells in malignant lymphomas), has been possible due to the high resolution and sensitivity provided by the development of flow cytometry. The flexibility, sensitivity, and accuracy of flow cytometry not only allows detection of cell populations which occur in small numbers, but also offers the opportunity to quantitate fluorescence intensity and epitope expression at extremely low levels (e.g., 3400 FITC molecules).

Within the past few years, many new functional sub-populations of cell types have been indentified and studied in heterogeneous hematopoietic and lymphoid human cell populations. Recent efforts have been directed toward determining the percentage of each particular sub-population present and the use of this variable as a diagnostic tool to distinguish between normal and malignant cells. It has been shown, for example, that changes in the T4/T8 (helper/supressor) ratio of lymphocytes, as well as total T4 cells, have a high correlation with certain stages in the progression of Acquired immune Deficiency Syndrome (AIDS).

The recognition of the clinical relevance of the availability of antibody binding sites and/or antibody binding site density per cell is at a very early stage of dvelopment. Quantitation of specific antibody binding sites on certain cells will have increasing utility and importance in clinical diagnosis as early indicators of the onset of a particular disease, as well as in monitoring the dosage and toxicity of certain drugs and the efficacy of treatment regimes. Quantitation of the antigenic sites may also provide a useful index of the progression and/or remission of immune related disease.

Presently, efforts to quantitate cellular epitopes have been significantly limited by the lack of standard reagents that will allow quantitation and accurate interpretation of the fluorescence signals. At best, determination of the number of antibody binding sites per cell is an extremely difficult technique to accomplish and thus, has remained a research methodology. For example, direct radio-binding assays have been used to quantitate the number of monoclonal antibodies to cells in research laboratories. This method is extremely tedious, however, and requires the incorporation of gamma-emitting iodine isotopes which are a biohazard requiring special laboratory facilities and licenses. Moreover, the cost of the methodology is high due to the equipment required and the short half-life of the iodine isotopes. These factors have seriously limited the utilization of this methodology in the clinical laboratory.

Theoretically, the number of antibody binding sites per cell can be assessed using flow cytometry. One methodology would involve calibrating the fluorescence channels of the instrument in terms of absolute numbers of molecules of fluorescent dye and also determining the average number of fluorescence dye molecules conjugated to the antibody molecule, usually referred to as the F/P ratio. In this manner, the average number of antibodies binding to cells could be calculated by determining the total number of fluorescent dye molecules associated with a particular antibody-labeled cell (via the instrument calibration) and dividing by the F/P ratio. The underlying assumption is that antibody binding at saturation is monovalent.

Unfortunately, this simplistic approach does not take into account the environmental conditions and instrument parameters that affect the measurement of fluorescence intensity of fluorochromes, such as pH of the suspension medium, quenching resulting from molecule to molecule proximity, changes in extinction coefficient due to binding and the selection of barrier filters and gains. Consequently, to determine absolute numbers of fluorochrome molecules present, "corrected fluorescence emission spectra" must be obtained based on many correction factors and quantum efficiencies. Such determinations and calculations are also tedious and extremely time consuming. This is perhaps the primary reason that antibody quantitation by means of fluorescence is not clinically practical and has remained a research methodology.

Recognizing such limitations, a series of products called Quantitative Fluorescent Microbead Standards Kits TM, commercially available from Flow Cytometry Standards Corporation (Research Triangle Park, N.C.) have been developed which provide for the quantitation of fluorescence intensity in terms of equivalent soluble fluorescent molecules, rather than absolute numbers of fluorescent molecules. This approach focuses on the relative intensity of the fluorescence signal of a sample compared to soluble solutions of the specific dye under controlled environmental conditions. The underlying premise is that their fluorescence intensities will maintain a direot quantitative relationship, when the excitation and emission spectra of the sample and solution match, and both are measured under the same environmental conditions and instrument settings.

Moreover, a standard particle with spectra matching the solution of the dye, will hold the same quantitative relationship with other particles, e.g., fluorescent antibody-labeled cells, as long as the fluorescent spectra of the sample match that of the standard particle and the dye solution. This criterion renders the fluorescence intensity measurements independent of the instrument settings, filters, and environmental factors, as long as the standard particles and the samples are measured under similar conditions. This method eliminates the need for the above mentioned correction factors since the number of molecules of fluorochrome present are no longer the determinant, but rather the fluorescence intensity of the particular sample relative to a soluble solution of the fluorochrome of a known concentration.

Recently, a special microbead capable of binding a calibrated number of antibodies has become available under the tradename Simply Cellular TM Microbeads (Flow Cytometry Standards Corporation, Research Triangle Park, N.C.). Briefly, with this product the number of antibody binding sites in a cell can be determined by first calibrating the fluorescence detector of the flow cytometer with the aforementioned quantitative microbead standards (Quantitative Fluorescent Microbead Standards Kit TM) and constructing a calibration plot of instrument response (i.e., channel number) as a function of equivalent soluble fluorescent molecules. Subsequently, an aliquot of the Simply Cellular TM Microbeads is saturated with the fluorescent monoclonal antibody to be studied using direct or indirect immunofluorescence methods and its fluorescence intensity determined against the calibration plot. The "effective fluorescence F/P ratio" is calculated by dividing the fluorescence intensity in terms of equivalent soluble fluorescent molecules by the number of antibody molecules binding to the Simply Cellular TM Microbeads (this information is provided by the manufacturer). Cell samples to be examined are also saturated with the same fluorescent monoclonal antibody under the same environmental conditions used with the microbeads and are analyzed with the flow cytometer using identical instrument settings. The fluorescence intensity of the cell samples is determined against the calibration plot and the average number of antibodies binding to the cell calculated by dividing the fluorescence intensity of the antibody-cell complex by the previously calculated "effective fluorescence F/P ratio".

This method of quantitating antibody binding has been found to be reliable. The utilization of this method in the clinical laboratory, however, will be limited by the number of steps involved in the procedure and the requirement of a specific set of Quantitative Fluorescent Microbead Standards that matches the excitation and emission spectra of the fluorochrome (e.g., fluorescein, phycoerythrin, Texas red, allophycocyanine, etc.) conjugated to the monoclonal antibody to be evaluated.

It is therefore an object of the present invention to provide a simple and readily conducted method for calibrating a flow cytometer or a fluorescence microscope directly in terms of number of binding antibodies as a function of fluorescence intensity value measured on the flow cytometer or fluorescence microscope.

It is another object of the invention to provide a calibration method of the type described in the preceding paragraph, which provides a direct relationship between instrument response and numbers of binding antibodies, independent of the conjugated fluorochrome. It is a further object of the invention to provide a microbead calibration kit for carrying out the above-referenced method of calibrating a flow cytometer or fluorescence microscope. Other objects and advantages will be more fully apparent ensuing disclosure and appended claims.

SUMMARY OF THE INVENTION

In one aspect, the present invention relates to a microbead calibration kit for calibrating a flow cytometer or fluorescence microscope in terms of number of binding antibodies as a function of fluorescence intensity value measured on the flow cytometer or fluorescence microscope, for subsequent measurement of a sample to which the same antibodies are bindable, such calibration kit comprising:

(a) set of populations of highly uniform same-sized microbeads having a coefficient of variation of diameter of about 2 percent or less, with the size of the microbeads being substantially equivalent to the size of the sample to be measured;

(b) at least two populations of the set of populations being capable of directly or indirectly binding a fluorescently labeled antibody, wherein the number of fluorescently labeled antibodies binding to each microbead in the at least two populations is the same within a said population thereof, but different from population to population among the respective said populations; and (c) another population of microbeads in the set, characterized by the same fluorescence spectra and fluorescence intensity as the sample prior to binding of fluorescently labeled antibodies thereto, such microbead population being selected from the group consisting of blank microbeads and autofluorescent microbeads.

In the above description of a microbead calibration kit according to the present invention, the phrase "directly or indirectly binding" in reference to microbeads and associated fluorescently labeled antibodies is intended to be broadly construed to encompass covalent bonding of the fluorescently labeled antibody directly to the microbead, i.e., "direct binding", as well as microbead systems wherein a linking group e.g., an immunological agent such as a protein or hapten is covalently bonded to the microbead, and the fluorescently labeled antibody is in turn covalently bonded or otherwise bound to this linking group, i.e., "indirect binding." Thus, for example, indirect binding may be effected by covalently bonding to the microbead a primary non-fluorescent antibody with which a secondary fluorescently labeled antibody is covalently bondable, i.e., the secondary fluorescently labeled antibody being a conjugate of the primary non-fluorescent antibody.

In another aspect, the present invention relates to a method for calibrating a flow cytometer or fluorescence microscope method in terms of number of binding antibodies as a function of fluorescence intensity value measured on the flow cytometer or fluorescence microscope, and subsequent measuring of a sample to which said antibodies are bindable, comprising the steps of:

(i) providing a microbead calibration kit comprising a set of populations of highly uniform same-sized microbeads having a coefficient of variation of diameter of about 2 percent or less, with said size of said microbeads being substantially equivalent to the size of the sample to be measured, said populations being capable of directly or indirectly binding a fluorescently labeled antibody, wherein the number of fluorescently labeled antibodies binding to each microbead in said populations is the same within a said population, but different from population to population among the respective populations in the set;

(ii) contacting each of the populations of microbeads with a fluorescently labeled antibody to effect direct or indirect binding of the antibody to the microbeads for saturation of the binding sites associated with the microbeads, to produce antibody-bearing microbeads having directly or indirectly bound thereto antibodies of known determinable number per microbead;

(iii) running each of the populations of antibody-bearing microbeads on the flow cytometer or fluorescence microscope, and determining the fluorescence intensity of each such population of antibody-bearing microbeads;

(iv) constructing a calibration plot of number of fluorescently labeled antibodies as an instrument response, as a function of fluorescence intensity measured on the flow cytometer or fluorescence microscope for the antibody-bearing microbeads;

(v) contacting said sample with a second portion of said fluorescently labeled antibody capable of binding to said sample, to yield a fluorescently labeled antibody-bearing sample;

(vi) running said fluorescently labeled antibody-bearing sample on said flow cytometer or fluorescence microscope and determining the fluorescence intensity of said sample; and (vii) determining from said calibration plot the number of fluorescently labeled antibodies binding to the sample, based on the fluorescence intensity of the sample measured on said flow cytometer or fluorescence microscope.

The present invention in still another aspect relates to a method for monitoring the status of an antigenic cellular condition, comprising calibrating a flow cytometer and measuring the number of antibodies binding to a cellular sample, according to the method above described, and thereafter repeating the determination of number of antiboiies binding to a successively obtained cellular sample, to establish the progressionary character of the antigenic cellular condition in a host from which the cellular samples are taken. The antigenic cellular condition may for example be Acquired Immune Deficiency Syndrome (AIDS) and the cellular samples may comprise T4 and T8 lymphocytes.

Other aspects and features of the invention will be more fully apparent from the ensuing disclosure and appended claims.

DETAILED DESCRIPTION OF THE INVENTION, AND PREFERRED EMBODIMENTS THEREOF

The disclosures of my prior co-pending U.S. patent applications, U.S. Patent Application Ser. No. 07/128,786 filed Dec. 4, 1987, and issued Aug. 15, 1989 as U.S. Pat. No. 4,857,451; U S. Patent Application Ser. No. 06/805,654 filed Dec. 11, 1985, and issued Sept. 27, 1988 as U.S. Pat. No. 4,774,189; U.S. Patent Application Ser. No. 06/685,464 filed Dec. 24, 1984, and issued Sept. 27, 1988 as U.S. Pat. No. 4,774,180; and U.S. Patent Application Ser. No. 06/850,746 filed Apr. 11, 1986, and issued May 9, 1989 as U.S. Pat. No. 4,828,984, are hereby incorporated by reference herein.

The microbead calibration kit useful in the broad practice of the present invention, for calibrating a flow cytometer or fluorescence microscope in terms of number of binding antibodies as a function of fluorescence intensity value measured on the flow cytometer or fluorescence microscope, includes a set of populations of highly uniform same-sized microbeads having coefficient of variation (CV) of diameter of about 2 percent or less, with the size of the microbeads being substantially equivalent to the size of the sample, e.g., biological cells, to be measured.

At least two populations of such set of populations of microbeads are capable of directly or indirectly binding a fluorescently labeled antibody. The number of fluorescently labeled antibodies binding to each microbead in such populations is the same within a single given population of the set, but is different from population to population among the respective constituent populations in the set.

It may also be desirable to include in such calibration kit for instrument baseline calibration purposes, another population of microbeads characterized by the same fluorescence spectra and fluorescence intensity as the sample prior to fluorescent labeling thereof, i.e., prior to directly or indirectly binding a fluorescently labeled antibody thereto. Such additional microbead population may be a population on blank microbeads, or alternatively it may comprise a population of auto-fluorescent microbeads.

Blank microbeads if employed in the microbeads calibration kit will not carry any fluorescent material associated therewith. The signal detected in the fluorescence channels of the flow cytometer or as detected by the fluorescence microscope from such blank microbeads will be due to stray light from the objects and/or electronic noise in the instrument. As used herein, the term "instrument" means flow cytometer and/or fluorescence microscope. If the samples being measured do not carry any fluorescent material prior to being labeled with the fluorescent antibodies, the fluorescence signal of the un-labeled samples as detected by the instrument should match that of the blank microbeads.

This may not be the case, however, with some samples carrying varying amounts of indigenous fluorescent materials, e.g., biological cells containing riboflavin, which is fluorescent in character. When the sample contains such indigenous fluorescent material, the sample is considered to be auto-fluorescent. Relatively high levels of auto-fluorescence have been observed in hepatic cells and in various cells in culture. When the samples to be measured are auto-fluorescent in character, the microbead calibration kit will desirably contain auto-fluorescent microbeads in addition to or in lieu of the aforementioned blank microbeads.

In use, the blank or auto-fluorescent microbeads are run initially on the flow cytometer or fluorescence microscope to determine the fluorescence intensity thereof as an instrument response to establish a fluorescence intensity baseline for further calibration measurement with the antibody-bound microbeads. In this manner, the optical and/or electronic anomalies of the instrument, and/or the auto-fluorescence of the samples to be measured can be taken into account in establishing the fluorescence intensity baseline, so that the antibody-bound microbeads subsequently are suitably quantitated.

As used herein, the term "antibody-bearing microbead" is intended to be broadly construed to encompass microbeads having antibodies directly or indirectly bound thereto, consistent with the previous discussion of direct and indirect binding of antibodies in the "Summary of the Invention" section hereof.

In the use of the above-described calibration kit, the microbead populations capable of directly or indirectly binding a fluorescently labeled antibody are contacted with the fluorescently labeled antibody, to effect direct or indirect binding of the antibody to the microbeads, for saturation of the binding sites associated with the microbeads. Such labeling produces microbeads having directly or indirectly bound thereto antibodies of a fluorescent character. The antibody may be fluorescently labeled by dye staining with a conventional dye, such as for example, fluorescein, phycoerythrin, Texas Red, allophycocyanine, etc.

Each of the resulting populations of antibody-bearing microbeads are then run on the flow cytometer or fluorescent microscope, and the fluorescence intensity of each population of labeled microbeads is determined.

From this fluorescence intensity data for each population, a calibration plqt of number of fluorescently labeled antibodies is plotted as a function of fluorescence intensity measured on the flow cytometer or fluorescence microscope for the antibody-bearing microbeads.

Once the calibration plot has been constructed, the sample to be measured is contacted with a fluorescently labeled antibody capable of binding to the sample, to yield a fluorescently labeled antibody-bearing sample, wherein the fluorescent labeling material is the same as previously employed for labeling the various microbead populations.

The fluorescent labeled antibody-bearing sample then is run on the flow cytometer or fluorescence microscope to determine the fluorescence intensity thereof. From such fluorescence intensity value of the sample, the number of fluorescently labeled antibodies binding to sample is determined from the calibration plot.

As applied to a flow cytometer, the calibration plot may be constructed in terms of number of binding antibodies as a function of the fluorescence intensity channels of the flow cytometer.

The highly uniform same-sized microbeads employed in calibration kits according to the present invention may suitably be formed in accordance with the synthesis method disclosed in my prior copending applications Ser. No. 06/685,464 filed Dec. 24, 1984 and Ser. No. 06/805,654, filed Dec. 11, 1985, the subject matter of which is hereby incorporated herein by reference. Suitable methodology for binding monoclonal antibodies to microbeads, either directly, by covalently bonding thereof to the microbead surface, or indirectly, involving binding of an antibody to a linking moiety (which may for example be an antibody conjugate to the fluorescently labeled antibody), is described more fully in my prior copending application Ser. No. 06/850,746 filed Apr. 11, 1986, the disclosure of which is also hereby incorporated by reference herein.

In general, quantitative comparison of the fluorescence of unknowns with standards is valid if two conditions are met. First, the excitation and emission spectra of the standards and unknowns, respectively, must be equivalent. Second, the instrument, settings, and barrier filters need to be the same for all the measurements.

This hypothesis provides a basis for using fluorescence instrument responses to directly determine the number of antibody binding sites on cells, provided that standards are available which behave as cells and bind known quantitites of the same fluorescent antibody used to label the cells. These standards need to have the same excitation and emission spectra as labeled cells, since they are binding the same antibodies under the same conditions. Such standards eliminate the need to determine numbers of dye molecules on a cell and F/P ratios of fluorescently conjugated antibodies. Instead, fluorescence intensity drops out of the algorithm and methodology as a "dummy variable," so that instrument response can be plotted directly as a function of the number of fluorescent antibodies.

The calibration kit of the invention comprises a set of highly uniform non-fluorescent particles that have the capacity to directly or indirectly bind pre-determined amounts of fluorescent antibodies. The fluorescent response of a flow cytometer or fluorescence microscope to these particles, saturated with a particular fluorescent-conjugated antibody, is thus used with these particles as standards to construct calibration plots. These plots are then used directly to determine the number of the same fluorescent antibody bound to cells.

Figure 1:
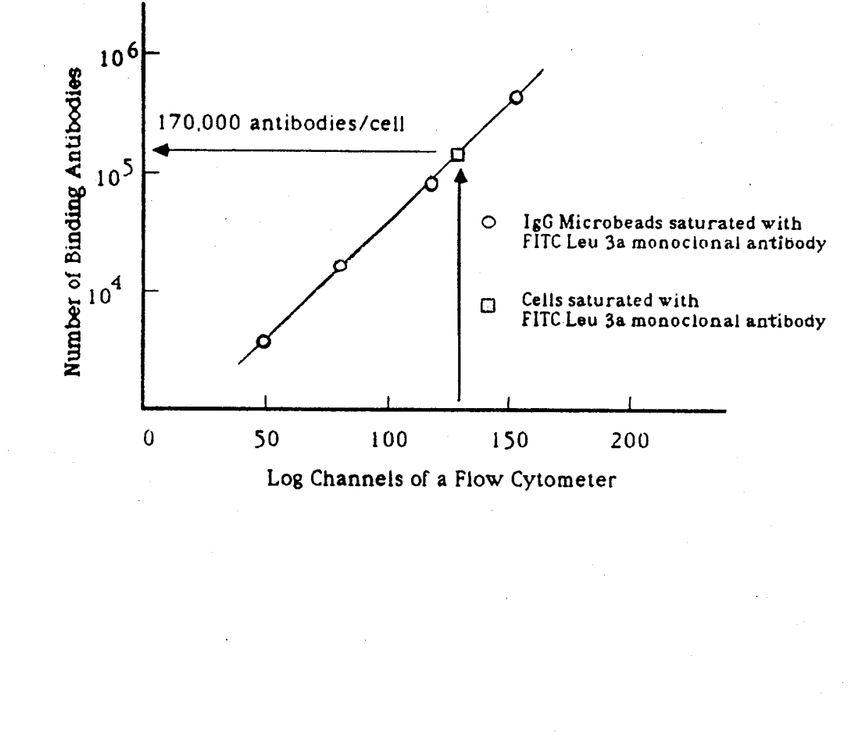
The single drawing is a calibration plot of number of binding antibodies, as a function of fluorescence intensity channels of a flow cytometer.

An example of this determination of the number of antibodies binding to a cell population is shown on the calibration plot of the sole Figure hereof, wherein number of binding antibodies are plotted as a function of the fluorescence intensity channels of a flow cytometer.

This plot was constructed using a set of microbeads in which each microbead population binds a different amount of antibody. Subsequently, cells saturated with the same fluorescent antibody are run on the instrument to generate a fluorescence intensity value from which the number of binding antibodies for the cellular sample can be read from the plot, as illustrated in the Figure.

As an illustrative example of a kit of the invention, a "Universal Mouse Monoclonal IgG Antibody Microbead Calibration Kit" may be provided containing five populations of highly uniform lymphocyte-sized microbeads, e.g., 8–10 microns in diameter. Four of these microbead populations will have the capacity to bind different known amounts of mouse IgG monoclonal antibody. The fifth population of microbeads will have no antibody binding capacity and will serve as a control blank to determine specificity and sensitivity of the system. With this microbead kit, calibration curves of direct antibody binding of any fluorescent mouse monoclonal antibody to cells may be made for flow cytometers and fluorescence microscopes. The mouse IgG monoclonal system is advantageously employed for the microbead calibration kit of the invention because most research and commercial diagnostic anti-human monoclonal antibodies are IgG isotypes and produced in mice. It will nonetheless be appreciated that numerous other kits are possible in the broad practice of the invention, for other antibody systems.

In the production of the microbeads calibration kit, a batch of microbeads may be synthesized with functional groups on their surface to which antibodies may be covalently bound, e.g., surface carboxyls that can be activated by water soluble carbodiimides to bind the antibodies. Four portions of the microbeads may for example be conjugated to four different amounts of whole polyclonal goat anti-mouse antibody. The polyclonal goat anti-mouse antibody bound to the microbeads is balanced to react against all the IgG isotypes equivalently. The fifth portion of micrqbads may be conjugated to a non-antibody binding protein, e.g., BA, and serve as the control blank.

The bonding capacity of each population of microbeads for mouse IgG monoclonal ahtibody in the above-described kit may be calibrated with non-fluorescenl 1-125 labeled mouse monoclonal antibodies. Calibration may be checked by both simple saturation determinations (as performed when staining cells) and by Scatchard Analysis. This binding calibration may suitably be carried out with at least three different mouse monoclonal antibody IgG isotypes, e.g., $IgG_1$, $IgG_{2a}$, and $IgG_{2b}$, with the specific isotypes advantageously being chosen according to which commercial diagnostic monoclonal isotypes are most readily available.

Thus, the kit of the invention may suitably contain a series of microbead populations having the capacity to bind different specific amounts of mouse IgG monoclonal antibodies, wherein the quantitative microbead antibody binding kit serves as a "universal reagent" in the determination of the number of antibody binding s-ites per cell by flow cytometry. The kit may be used with all mouse IgG monoclonal antibodies regardless of the fluorochrome conjugated to them. Such kit as indicated, may consist of a set of five populations of highly uniform cell-sized (8-9 microns in diameter) microbeads; four of these populations will behave as "model lymphocytes" in terms of size and general antigenic activity while the fifth microbead population will be a blank to assess the degree of non-specific labeling and the sensitivity of the instrument.

The fluorescence intensity reading of a flow cytometer can be rapidly and easily calibrated by saturating an aliquot of each microbead population in the kit with the moloclonal antibody to be used to label the cell samples and plotting the modal peak channel for each population of microbeads against the calibrated number of binding sites for that population. The latter value for each population of microbeads may be assessed by the kit manufacturer using radio-binding techniques. This calibration plot will provide a direct relationship between instrument response and numbers of binding antibodies, independent of the conjugated fluorochrome. No intermediate quantitative fluorescence standards are needed in this calibration.

The various clinical and research applications of the kit of this invention include correlating changes in the number of surface epitopes with the onset, progression and/or remission of specific immune diseases. In addition, the kit may be utilized as a quality control reagent for the fluorescence stablility of fluorescent antibodies.

The clinical applicability of the calibration kit of the invention includes applications permitting pathologists, immunologists, and onocologists to achieve a better and more accurate diagnosis, treatment and prognosis of immune related diseases such as malignant lymphomas and lymphoid leukemias, acquired immune deficiency disease, cadaveric organ transplantation, and multiple sclerosis. Quantitative functional analysis combined with cell phenotyping may thus assist clinical immunologists in monitoring and adjusting immunotherapeutic treatments in an easy, simple, and reliable manner.

An even more useful application of the quantitation of antigenic sites arises in the detection of auto-antibodies. Several diseases are caused by the presence of auto-antibodies on the surface of cells, resulting in cell dysfunction and destruction. The most well-known examples are: auto-immune hemolytic anemia, neutropenta, and thrombocytopenia. In all of these conditions, the measurement of the amount of antibody bound to the surface of the affected cells (i.e., red blood cells, neutrophils, and platelets; respectively) is of extreme clinical relevance for diagnosis, treatment and prognosis. The use of flow cytometry in combination with the quantitative microbead antibody binding kit of the invention provides a methodology which has the potential to contribute significantly to the improvement of human health care.

The features of and advantages of the invention are more fully shown hereinafter with reference to the following non-limiting examples, wherein all parts and percentages are by weight, unless otherwise expressly stated.

EXAMPLE I

This example illustrates a methodology for detection of membrane antigen in microbead and cell suspension by using both direct and indirect staining techniques.

Direct Staining Technique

Using this technique, 100 ul of the cell or microbead suspension ($1-2 \times 10^7$ cells or microbeads/ml) are mixed with 20 ul fluorescent-conjugated monoclonal antibodies ( 50 ug monoclonal antibody/ml). After a 30 min incubation period at 4° C. cells or microbeads are washed twice with PBS by centrifugation, resuspended in PBS and subjected to flow cytometry analysis. To eliminate erythrocytes from the cell samples, 2 ml of lysing agent (Becton Dickinson & Co.) is added to the antibody-labeled cells and incubated prior to washing with PBS.

Indirect Staining Technique

For the indirect staining procedure, cells and microbead suspensions are first incubated as described above with a primary corresponding unconjugated monoclonal antibody. Following incubation, cells and microbeads are washed twice with PBS and resuspended to volume with fresh PBS solution containing 1% BSA and 10% fetal calf serum. The cells or microbeads, previously reacted with the primary antibody, are then incubated with 20 ul of a secondary fluorescenated antibody conjugated to goat anti-mouse IgG F(ab')2 (CalTag, Inc.). After a 30 min incubation at 4° C., cells or microbeads are washed twice with PBS by centrifugation, resuspended in PBS and subjected to flow cytometry analysis. Antibody-labeled cells are incubated with 2 ml lysing reagent for 10 minutes prior to PBS wash and flow cytometry analysis.

EXAMPLE II

Flow Cytometry Analysis

Flow cytometry analysis is performed on an Epics V flow cytometer (Coulter Electronics, Hialeah, FL) set-up with a 2 watt Argon laser, a 520-550 BP nm barrier filter for the "green" fluorescence channel, a 560 LP nm barrier filter for the "red" fluorescence channel, and a logarithmic amplifier. Alignment and calibration of the instrument are performed using Quantitative Fluorescent Microbead Standard Kits (Flow Cytometry Standards Corporation, Research Triangle Park, N.C.) as described in the kit's technical brochure. Microbead and cell samples are analyzed at 500 mW output of the 488 nm laser line and the PMT voltages are adjusted so as to place a standard benchmark microbead from the kit in a specific fluorescence channel, e.g., the No. 2 microbead of the fluorescein kit ($1.8 \times 10^5$ eq. sol. fl/bead) in FL1 channel 200. The % CV of the histograms is monitored to ensured optimum alignment.

EXAMPLE III

Construction of Flow Cytometry Calibration Plots

The following procedure is used to calibrate the flow cytometer with both the Quantitative Fluorescence Microbead Standards Kits and the microbeads calibration kit of the present invention. The modal channel number for each population of fluorescent microbeads is determined from the histogram generated after collecting data from 10,000 microbeads of the singlet population gatd on dot plot of the forward and side-scatter signals. When using the log amplifier, the calibration plot is constructed on semi-log paper by plotting the modal channel against the calibrated value for the corresponding microbead population. For the Quantitative Fluorescent Microbead Standards Kits, the calibrated value (fluorescence intensity in terms of equivalent fluorescent soluble molecules per microbead) is printed on the label. For the antibody coated-microbeads of the calibration kit, the calibrated value (number of IgG monoclonal antibody binding sites per microbead) is derived from radio-binding studies. When using linear amplifiers the calibration plots are constructed on log-log paper.

EXAMPLE IV

Synthesis of the Highly Uniform Microbeads

Highly uniform microbeads (8–10 microns in diameter) are synthesized by microbead seed swelling techniques as described in U.S. Pat. No. 4,714,682. This method involves the incorporation of a highly water insoluble component (e.g., hexadecane) into the microbeads before swelling the microbead seeds with water insoluble monomers, (e.g., styrene), and a water insoluble thermal initiator (e.g., AIBN). Polymerization of the swollen microbeads is accomplished by raising the temperature to 70° C. under nitrogen. The resulting monodispersed microbeads are washed with 0.1% aqueous SDS solution to remove homopolymer and small secondary microbead populations.

The polymerization mixture contains 5–10% of a momomer which has an epoxy group (e.g., glycidyl methacrylate) that will serve as the primary active surface group to which compounds having other specific chemical groups may be attached. The epoxy containing microbeads are suspended in 1 M glycine solutions at pH 9.5 for 12 hours to covalently bind the primary amine of the glycine to the epoxy groups of the microbeads. This linkage provides a peptide-spacer to which the antibodies may later be covalently bound via activation with water soluble carbodiimide of the corboxyl group of the glycine molecule.

To assess the size and uniformity (% CV) of the microbeads, the forward angle light-scatter channel of a flow cytometer is calibrated with a series of similar microbeads of calibrated size (Quantitative Fluorescein Microbead Standard Kit TM, Flow Cytometry Standards Corporation, Research Triangle Park, N.C.). This quantitative kit contains 5 different populations of microbeads, ranging in size from 4.4 to 9.0 microns in diameter.

EXAMPLE V

Surface Coating of the Microbeads

After synthesizing the lymphocyte-sized microbeads, immunoproteins are covalently bound to their surface to provide the necessary antigenic activity. Two types of immunoproteins are employed: (1) a polyclonal goat anti-mouse balance to bind IgG1, IgG2a, IgG2b (Cal-Tag, Inc.), and (2) a monoclonal rat anti-mouse kappa specific antibody (Becton Dickinson Co.).

Covalent binding of. antibodies to the microbeads is accomplished via first activation of the carboxyl groups of the glycine on the microbead surface with a water soluble carbodiimide, e.g., [1-Ethyl-3-(3-dimethylaminopropyl) carbodiimide.HCl]in a 0.05 M HEPES buffer at pH 4.5. Subsequent covalent binding of the antibody to the microbeads is conducted by washing and resuspending the microbeads in 0.05 M HEPES buffer (pH 7.0) containing the antibody ( 0.1 mg/ml.) for 12 hours. The amount of antibody to be covalently bound to the activated carboxyl groups on the microbeads is controlled by either limiting the amount of antibody being exposed to the activated microbeads, or by mixing specific proportions of a non-interactive protein, e.g., Bovine Serum Albumin (BSA), with the antibody to provide a competitive reaction, thus limiting the amount of antibody binding to each microbead. Four microbead populations differing in the amount of antibody bound are produced. A fifth portion of microbeads is conjugated o a non-antibody binding protein, e.g., BSA, and serves as the control blank. Quenching of any remaining activated carboxyl groups and elimination of non-specific binding of antibodies to the microbeads is accomplished by resuspension and storage of the microbeads in PBS (pH 7.2) containing 0.5% BSA.

EXAMPLE VII

Determination of the Average Number of Antibody Binding Sites on Specific Sub-populations of Lymphocytes A series of mouse monoclonal antibodies acquired from different sources which bind to specific cell-cluster types in normal human blood are.evaluated. The number of antibody binding sites for CD2, CD4, and CD8 lymphocytes is determined against a calibration plot for a flow cytometer which is constructed using the coated microbeads of the kit of the present invention, and different fluorescent conjugated monoclonal antibodies. The specific commercial fluorescent antibodies tested are summarized in Table I.

TABLE I

| Antigen Cluster | MonoclonalAB | Isotype | Source |
| --- | --- | --- | --- |
| CD2 | Leu-5b | IgG2a,k | Becton Dickinson |
|  | OKT11 | IgG2a | Ortho Diagnostic |
|  | CCT11 | IgG1,k | Coulter Corporation |
| CD4 | Leu-3a | IgG1,k | Becton Dickinson |
|  | OKT4 | IgG2b | Ortho Diagnostic |
|  | CCT4 | IgG1,k | Coulter Corporation |
| CD8 | Leu-2b | IgG2a,k | Becton Dickinson |
|  | OKT8 | IgG2a | Ortho Diagnostic |
|  | CCT8 | IgG1,k | Coulter Corporation |

Aliquots of each microbead population are incubated with saturating concentrations of each fluorescent monoclonal antibody and analyzed in a flow cytometer. A calibration plot is constructed for each specific fluorescent monoclonal antibody using the modal channel of fluorescence intensity of each antibody-labeled microbead population and the corresponding number of calibrated antjbody binding sites, as previously determined. Aliquots of whole blood are also incubated with each of the monoclonal antibodies under the same experimenal conditions followed by lysing and washing before anaylsis. The amount of antigen expression by CD2, CD4 and CD8 lymphocytes is determined against the calibration plots constructed from modal peak channels from the microbeads saturated with each corresponding antibody.

While the invention has been described with reference to specific embodiments, it will be appreciated that numerous other variations, modifications, and embodiments are possible, and accordingly all such variations, modifications, and embodiments are to be considered as being within the spirit and scope of the present invention.

What is claimed is:

1. A microbead calibration kit for calibrating a flow cytometer or microscope in terms of the number of binding antibodies per microbead as a function of fluorescence intensity value measured on the flow cytometer of fluorescence microscope, for subsequent measurement of a sample to which the same antibodies are bindable, said calibration kit comprising:
    (a) a set of populations of microbeads having a coefficient of variation of diameter of about 2 percent or less, with said diameter of said microbeads being substantially equivalent to the diameter of the sample to be measured;
    (b) at least two populations of said set of populations being capable of binding, directly or via a linking group, a fluorescently labeled antibody, wherein the number of fluorescently labeled antibodies binding to each microbead in said at least two populations is the same within a said population thereof, but different from population to population among the respective said populations;
    (c) another population of microbeads in said set, having the same fluorescence spectra and fluorescence intensity as said sample prior to binding of fluorescently labeled antibodies thereto, said microbead population being selected from the group consisting of blank microbeads and auto-fluorescent microbeads; and
    (d) container means enclosing each of said populations of microbeads.

2. A microbead calibration kit according to claim 1, wherein said at least two populations comprise microbeads having covalently bouded thereto a linking group consisting of immunological agent capable of binding to said fluorescently labeled antibody.

3. A microbead calibration kit according to claim 2, wherein said immunological agent covalently bonded to said microbeads is selected from the group consisting of: polyclonal goat anti-mouse antibodies; polyclonal rat anti-mouse antibodies; monoclonal anti-mouse kappa specific antibodies; and monovalent anti-mouse antibody fragments.

4. A microbead calibration kit according to claim 1, wherein said at least two populations are capable of binding a fluorescent mouse anti-human monoclonal antibody of IgG isotype.

5. A microbead calibration kit according to claim 1, wherein said set of populations of microbeads have a diameter in the range of from about 2 to about 15 microns in diameter.

6. A microbead calibration kit according to claim 1, wherein said set of populations of microbeads have a diameter in the range of from about 7 to about 10 microns in diameter.

7. A method for calibrating a flow cytometer or fluorescence microscope in terms of the number of binding antibodies per microbead as a function of fluorescence intensity value measured on the flow cytometer of fluorescence microscope, and subsequent measuring of a sample to which said antibodies are bindable, comprising the steps of:
    (i) providing a microbead calibration kit comprising a set of populations of microbeads having a coefficient of variation of diameter of about 2 percent or less, with said diameter of said microbeadebeing substantially equivalent to the diameter of the sample to be measured, said populations being capable of binding, directly or via a linking group, a fluorescently labeled antibody, wherein the number of fluorescently labeled antibodies, binding to each microbead in said populations is the same within a said population, but different from population to population among the respective said populations in said set;
    (ii) oontacting each of said populations of microbeads with a fluorescently labeled antibody to effect direct or indirect binding of said antibody to said microbeads for saturation of the binding sites associates with said microbeads, to produce antibody-bearing microbeads having directly or indirectly bound thereto antibodies of a known or determinable number per microbead;
    (iii) determining the fluorescence intensity of each of said populations of antibody-bearing microbeads on said flow cytometer or fluorescence microscope;
    (iv) constructing a calibration plot of the number of fluorescently labeled antibodies, as a function of fluorescence intensity measured on said cytometer of fluorescence microscope for said antibody-bearing microbeads;
    (v) contacting said sample with a second portion of said fluorescently labeled antibody capable of binding to said sample, to yield a fluorescently labeled antibody-bearing sample;
    (vi) determining the fluorescence intensity of said fluorescently labeled antibody-bearnng sample on said flow cytometer or fluorescence microscope; and
    (vii) determining from said calibration plot the number of fluorescently labeled antibodies binding to the sample, based on the fluorescence intensity of the sample measured on said flow cytometer of fluorescence microscope.

8. A method according to claim 7, wherein said method is applied to a flow cytometer, and said calibration plot is constructed in terms of number of binding antibodies as a function of the fluorescence intensity channels of said flow cytometer.

9. A method according to claim 7, wherein said antibody is a mouse IgG monoclonal antibody.

10. A method according to claim 7, comprising providing another population of microbeads having the same fluorescence spectra and fluorescence intensity as said sample prior to binding of fluorescently labeled antibody thereto, said microbead population being selected from the group consisting of blank microbeads and auto-fluorescent microbeads, and running said blank or auto-fluorescent microbeads on said flow cytometer or fluorescence microscope to determine the fluorescence intensity thereof as an instrument response, to establish a fluorescence intensity baseline for further calibration measurement with said antibody-bound microbeads.

11. A method according to claim 7, wherein said fluorescently labeled antibody is labeled with a fluorescent dye selected from the group consisting of fluorescein, phycoerthyrin, Texas red, and allophycocyanine.

12. A method according to claim 7, wherein said antibody is a mouse anti-human monoclonal antibody of IgG isotype.

13. A method according to claim 7, wherein said fluorescently labeled antibody is labeled with fluorescein.

14. A method according to claim 7, wherein said set of populations of microbeads comprise microbeads having a diameter of from about 2 to about 15 microns.

15. A method according to claim 7, wherein said set of populations of microbeads comprise microbeads having a diameter of from about 7 to about 10 microns.

16. A method according to claim 7, wherein said sample is selected from the group consisting of lymphocytes, red blood cells, neutrophils, and platelets.

17. A method according to claim 7, wherein said sample comprises lymphocytes.

18. A method of monitoring the variation in the number of available surface epitopes in successively obtained cellular samples to determine charge in immunologic status of a host from which said samples are obtained, comprising calibrating a flow cytometer and measuring the number of antibodies binding to a cellular sample, according to the method of claim 7, and thereafter repeating the determination of number of antibodies binding to a successively obtained cellular sample, to determine said change in immunologic status of said host from which said cellular samples are taken.

19. A method according to claim 18, wherein said immunologic status comprises the presence of acquired immune deficiency syndrome in said host and said cellular samples comprise T4 and T8 lymphocytes.

* * * * *

UNITED STATES PATENT AND TRADEMARK OFFICE
CERTIFICATE OF CORRECTION

PATENT NO. : 4,918,004

DATED : April 17, 1990

INVENTOR(S) : Abraham Schwartz

It is certified that error appears in the above-identified patent and that said Letters Patent is hereby corrected as shown below:

Column 4, line 4, insert --from the-- after "fully apparent".
Column 7, line 27, replace "plqt" with --plot--.
Column 9, line 3, replace "micrqbads" with --microbeads--; lines 8-9, replace "non-fluorescent 1-125" with --non-fluorescent I-125--; line 24, replace "s-ites" with --sites--; and line 37, replace "moloclonal" with --monoclonal--.
Column 10, lines 2-3, replace "neutropenta" with --neutropenia--.
Column 11, line 58, replace "corboxyl" with --carboxyl--.
Column 13, line 53, replace "bouded" with --bonded--.
Column 14, line 17, replace "microbeadbeing" with --microbeads being--; and line 27, replace "oontacting" with --contacting--.
Column 16, line 11, replace "charge" with --change--.
Column 9, line 7, "ahtibody" should be --antibody--.

Signed and Sealed this

Twenty-third Day of July, 1991

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,918,004
DATED : April 17, 1990
INVENTOR(S) : Abraham Schwartz

It is certified that error appears in the above-identified patent and that said Letters Patent is hereby corrected as shown below:

On the title page, at item (63), correct "4,774,180" to read --4,767,206--.

Column 1, line 17, correct "Sept. 27, 1988" to read --Aug. 30, 1988--.

Column 1, line 18, correct "4,774,180" to read --4,767,206--.

Column 6, lines 1-2, correct "Sept. 27, 1988" to read --Aug. 30, 1988--.

Column 6, line 3, correct "4,774,180" to read --4,767,206--.

Signed and Sealed this

Twenty-first Day of March, 1995

Attest:

BRUCE LEHMAN

Attesting Officer

Commissioner of Patents and Trademarks